(12) United States Patent
Witt

(10) Patent No.: US 9,618,485 B2
(45) Date of Patent: Apr. 11, 2017

(54) HPLC-SYSTEM WITH VARIABLE FLOW RATE

(75) Inventor: Klaus Witt, Keltern (DE)

(73) Assignee: Agilent Technology, Inc., Santa Clara, CA (US)

( * ) Notice: Subject to any disclaimer, the term of this patent is extended or adjusted under 35 U.S.C. 154(b) by 1415 days.

(21) Appl. No.: 12/742,098

(22) PCT Filed: Nov. 12, 2007

(86) PCT No.: PCT/EP2007/062198
§ 371 (c)(1),
(2), (4) Date: Jun. 23, 2010

(87) PCT Pub. No.: WO2009/062538
PCT Pub. Date: May 22, 2009

(65) Prior Publication Data
US 2010/0252502 A1    Oct. 7, 2010

(51) Int. Cl.
*B01D 15/08* (2006.01)
*G01N 30/32* (2006.01)
*F04B 11/00* (2006.01)
*G01N 30/22* (2006.01)
*G01N 30/24* (2006.01)
*G01N 30/86* (2006.01)

(52) U.S. Cl.
CPC .......... *G01N 30/32* (2013.01); *F04B 11/0058* (2013.01); *F04B 11/0075* (2013.01); *G01N 30/22* (2013.01); *G01N 30/24* (2013.01); *G01N 30/8658* (2013.01); *G01N 2030/324* (2013.01)

(58) Field of Classification Search
CPC .. G01N 30/32; G01N 30/22; G01N 2030/324; G01N 30/8658; G01N 30/24; G01N 30/02; G01N 30/36; B01D 15/163; B01D 15/166
See application file for complete search history.

(56) References Cited

U.S. PATENT DOCUMENTS

| 4,084,246 A | 4/1978 | Schwartz |
| 5,004,538 A * | 4/1991 | Apfel ..................... G01N 30/32 210/101 |
| 5,040,126 A * | 8/1991 | Allington ........................ 702/47 |
| 5,305,232 A | 4/1994 | Chimowitz et al. |
| 2005/0100464 A1 | 5/2005 | Maruyama |
| 2005/0121392 A1 | 6/2005 | Hoffmann |

(Continued)

FOREIGN PATENT DOCUMENTS

| CN | 1619305 A | 5/2005 |
| CN | 1627067 A | 6/2005 |

(Continued)

OTHER PUBLICATIONS

Office Action mailed Oct. 10, 2012 in Chinese Patent Application No. 200780101526.7.

(Continued)

*Primary Examiner* — Matthew O Savage

(57) ABSTRACT

In a high performance liquid chromatography system, wherein a mobile phase is driven through a stationary phase for separating compounds of a sample fluid comprised in the mobile phase, a flow rate of the mobile phase is controlled in dependence on a variation in a control value in the system.

9 Claims, 4 Drawing Sheets

(56) References Cited

U.S. PATENT DOCUMENTS

2006/0219618 A1* 10/2006 Witt et al. .................. 210/198.2
2008/0022765 A1*  1/2008 Witt et al. ...................... 73/199
2010/0252502 A1* 10/2010 Witt ............................. 210/656

FOREIGN PATENT DOCUMENTS

| EP | 0309596 B1    |   | 3/1993  |
|----|---------------|---|---------|
| EP | 1707958       |   | 10/2006 |
| EP | 001777515 B1  | * | 4/2007  |
| WO | 0177662 A2    |   | 10/2001 |
| WO | WO0188528     |   | 11/2001 |

OTHER PUBLICATIONS

Office Action mailed Nov. 3, 2014 in Chinese Patent Application No. 200780101526.7.
Office Action mailed Oct. 6, 2014 in European Patent Application No. 07822486.2.
Office Action mailed May 27, 2015 in European Patent Application No. 0782486.2-1408.
European Summons to attend oral proceedings dated Apr. 19, 2016 from related European Application No. 07822486.2.
International Search Report and Written Opinion dated Feb. 28, 2007 from related International Application No. PCT/EP2007/062198.

* cited by examiner

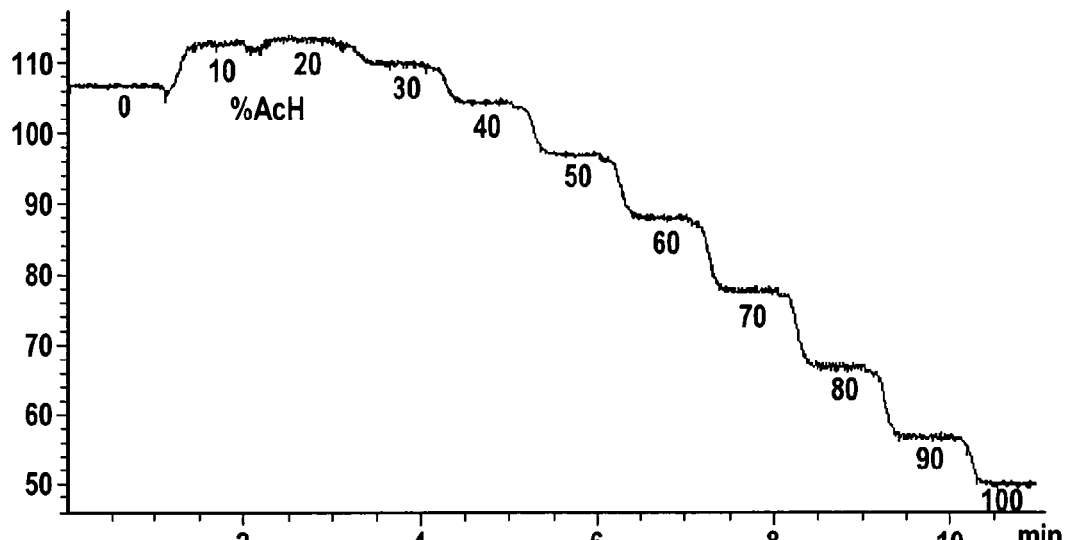
Fig. 5
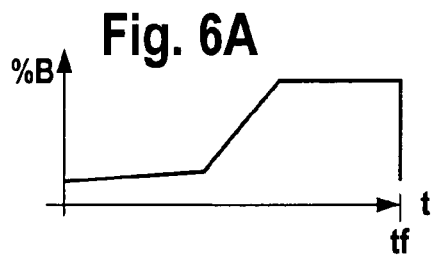
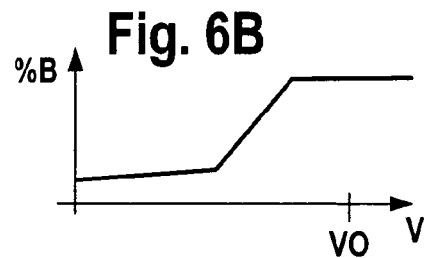
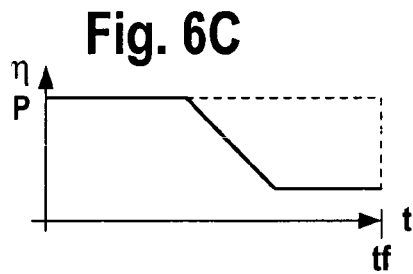
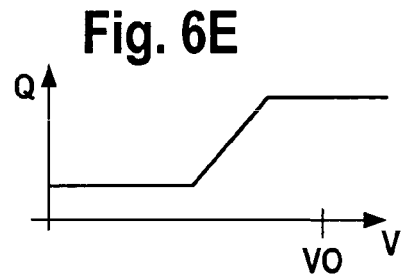
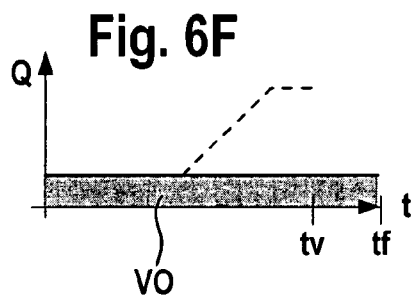
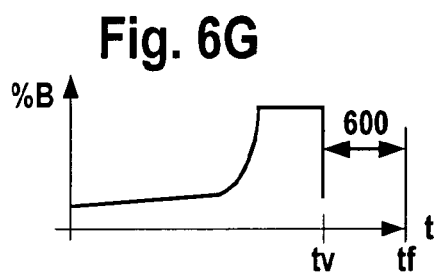

HPLC-SYSTEM WITH VARIABLE FLOW RATE

BACKGROUND ART

The present invention relates to high performance liquid chromatography.

In high performance liquid chromatography (HPLC), a liquid usually has to be provided at a very controlled flow rate (e.g. in the range of microliters to milliliters per minute) and at high pressure (typically 200-1000 bar, and beyond up to currently even 2000 bar, at which compressibility of the liquid becomes noticeable). Piston or plunger pumps usually comprise one or more pistons arranged to perform reciprocal movements in a corresponding pump working chamber, thereby compressing the liquid within the pump working chamber(s). In fluid dynamics and hydrometry, the volumetric flow rate (referred to herein as flow rate) is the volume of fluid which passes through a given surface per unit time, usually measured at the point of detection.

A liquid chromatography pumping system is described in EP 0309596 B1 by the same applicant, Agilent Technologies, depicting a pumping apparatus comprising a dual piston pump system for delivering liquid at high pressure for solvent delivery in liquid chromatography.

Modern LC-systems see changing requirements. In the interest to increase peak capacity (i.e. the total number of peaks per time interval) several parameters are optimized, such as smaller size of packing material, smaller inner diameter columns, faster linear speed of solutes during separation, faster compositional gradients, longer separation beds, etc. Most of these developments have in common that they increase the pressure drop needed to drive the liquid through the system.

HPLC systems often are operated in so-called gradient mode, wherein e.g. for reversed phase chromatography the organic content is ramped over time, or for ion exchange chromatography the salt content is ramped over time. Especially in proteomics most applications are based on water/acetonitrile gradients.

An analytical protocol for running a defined analytical process is called the "method". In the analytical protocol—or method—for a gradient separation, the gradient is specifically defined as a composition change (e.g. % B over time), while the flow rate is kept constant over the major part of such a method.

Increasing the pressure drop across a column may bring the method execution close to limits of the technical hardware. Modern LC-Systems already are designed to leverage all pressure capabilities of the given setup. To prevent overstress to certain components the system is often equipped with pressure sensing having shut-off features, which are designed to terminate operation before the hardware is damaged.

Column temperature might be increased in a quest to gain more headspace in pressure by reducing viscosity, thus reducing nominal pressure drop of a given column.

Chromatographic columns filled with smaller particles are susceptible to clogging, which goes back to either solid material from dirty samples injected or particles and abbreviates that might stem from seals or valves.

For chromatographers it is good laboratory praxis not to use all pressure reserve available right from start. Minor clogging of the column would then raise pressure above the shut-off limit. Often about 10-20% of the available maximum pressure range remains unused when optimizing the method, in particular to avoid measurement failures caused from temporarily exceeding shut-off limits.

DISCLOSURE

It is an object of the invention to provide an improved high performance liquid chromatography.

Embodiments of the present invention shall be illustrated the following. Headlines are used for easier comprehension but are not limiting in any sense.

A high performance liquid chromatography system usually comprises a separating device having a stationary phase for separating compounds of a sample fluid comprised in a mobile phase, and a mobile phase drive adapted for driving the mobile phase through the separating device.

According to embodiments of the present invention, a flow rate of the mobile phase is controlled in dependence on a variation in a control value, which may be related to a property (such as a pressure) of or in the mobile phase. While conventional HPLC systems usually follow the "paradigm" of operating at a constant flow rate, embodiments of the invention leave that paradigm and may vary the flow rate in response to variations e.g. in the mobile phase pressure. With departing from the concept of constant flow rates, it may now be possible to better utilize resources of the HPLC system. As an example, it may now be possible to cover (almost) the full available pressure range of the mobile phase drive, e.g. by operating the mobile phase drive to provide an essentially constant output pressure, which may be selected to be the maximum available pressure or close to (e.g. in order to maintain some reserve).

The HPLC system can be designed to be essentially self-controlled or free-wheeling, so that a variation in the control value, e.g. the pressure, "automatically" leads to a variation in flow rate. This can be achieved e.g. by (passively) operating the mobile phase drive to be free-wheeling, so that the mobile phase drive is running at a given power (e.g. maximum power). In such case, a variation in the mobile phase pressure will in turn lead to a variation in flow rate. For example when the pressure decreases, the free-wheeling mobile phase drive will then have some power left to increase the flow rate, as it can then run faster at the same power consumption. It is to be understood that in the constant flow rate operation mode as in conventional HPLC systems, such self-controlling or free-wheeling capability is usually disabled in order to ensure constant flow rate.

Alternatively, the mobile phase drive may also be actively operated to drive the mobile phase at a flow rate in dependence on the variation in the control value. In such case, e.g. a controller or control unit actively controls the mobile phase drive to vary the flow rate in response to a variation in the mobile phase pressure.

In either case, operating the mobile phase drive might comprise at least one of reducing the flow rate in response to an increase of the control value, and increasing the flow rate in response to a decrease of the control value. In preferred embodiments, at least one of the reduction and increase of the flow rate is in relation to a given (or set) value of the flow rate. Such value might be a defined flow rate value e.g. recommended, rated or otherwise defined for operating a certain type of stationary phase, for example the recommended or optimal (e.g. according to the Van-Deemter-Curve) flow rate for a certain type of chromatographic column. Often this defined flow rate is set such that the maximum expected pressure drop is still within the limits of what the system is capable of. In one embodiment, at least one of the reduction and increase of the flow rate follows a continuous function, a step-wise function, or a combination of both. In case of a step-wise function, not every variation in the mobile phase pressure will lead to a different value of the flow rate, but only if another range is reached, with each range being assigned to a certain value of the flow rate. The combined case may be a continuous function, which levels off when a certain maximum flow rate is reached.

In some embodiments, the mobile phase drive is working in cyclic manner and having a cycle period when delivering the mobile phase. This might result e.g. from a reciprocating movement of a component of the mobile phase drive, such as a piston reciprocating in a pump working chamber, so that the cycle period of the mobile phase drive is determined by the reciprocating movement. The mobile phase drive in such embodiments is then operated to respond only to such variation in the control value having a time constant larger than the cycle period. Thus, it can be ensured that the flow rate is not following pressure variations caused by the mobile phase drive itself. The time constant is preferably selected to be larger than ripples or pulsation resulting from the cycling operation of the mobile phase drive.

In case the mobile phase drive comprises an actuator, the flow rate of the mobile phase might be determined by monitoring a drive speed of the actuator of the mobile phase drive. In case the mobile phase drive comprises a piston pump, the flow rate might be determined by monitoring a displacement rate of the piston pump (as disclosed e.g. in the aforementioned EP 0309596 B1). In case the mobile phase drive comprises a feed forward pump, the flow rate might be determined by reading the commanded value. In case system comprises a flow sensor, the flow rate might be determined by measuring an actual flow rate by the flow sensor. In case the system comprises a mass flow sensor, the flow rate might be determined by measuring a mass flow by the mass flow sensor.

The flow rate of the mobile phase might be determined (e.g. as a mass flow) at an outlet of the mobile phase drive, before passing the separating device, after passing the separating device, at the point of detection, at an outlet of the high performance liquid chromatography system, or any combination thereof.

In one embodiment, the mobile phase drive is operated to maintain the control value to be substantially constant or at least within a given range, e.g. during the time of an analytical run. As pointed out above, this might allow to operate the mobile phase drive to deliver the mobile phase at a certain pressure, such as a maximum pressure, which might be the maximum achievable pressure of the mobile phase drive with or without a certain safety margin (to ensure that small pressure increases—e.g. at time constants shorter than the response time of the control system—will not lead to irregularities, such as measuring faults, shut-offs, etc.). Such operating at constant/maximum pressure, in turn, might lead to reduced analysis times required to separate certain compounds of the sample fluid. Also, this can ensure that the mobile phase pressure will not exceed its set control value (within certain boundaries resulting from setup times or short term pressure ripples), so that less safety margin is required and accordingly the mobile phase drive can be operated at higher control values. Certain columns may have pressure limits lower than the achievable pressure from the drive. In such cases the pressure can be controlled to a level that is originally specified for the column. In one embodiment the mobile phase drive can be operated at a pressure, which is adjusted such that a specific pressure drop is left across the column, which may be a sub-fraction of the system pressure.

In some embodiments, the control value is or is related to a pressure such as an actually measured (e.g. by a pressure sensor) or otherwise determined pressure in the mobile phase, a pressure difference such as a pressure difference along the stationary phase or the separating device, a control parameter of the mobile phase drive such as an electrical current, voltage and power for driving a pump, a value related to a viscosity of the mobile phase, or any combination thereof. In case of the control parameter of the mobile phase drive, a variation in current, voltage or power for driving the pump is usually indicative of the load of the pump or in other words of the pressure drop required for driving the mobile phase through the stationary phase.

In preferred embodiments, the control value is related to the (actual) pressure in the mobile phase at an outlet of the mobile phase drive, an injection point where the sample fluid is introduced into the mobile phase, an entrance area of the stationary phase or the separating device, where the mobile phase first enters the stationary phase, preferably a head of column in case the stationary phase comprises a chromatographic column, an exit area of the stationary phase or the separating device, where the mobile phase exits the stationary phase, preferably a column outlet in case the stationary phase comprises a chromatographic column, or a combination thereof.

Gradient Operation

Operating the mobile phase drive to maintain the control value to be substantially constant or at least within a given range might also turn out in particular useful when running the HPLC system in gradient mode, i.e. when composition of the mobile phase varies over time. In gradient mode, typically the mobile phase comprises different solvent components with the ratio of the different solvent components being varied over time. As an example in reversed phase HPLC, the mobile phase might be a mixture of water and acetonitrile, with the ratio of water to acetonitrile being varied from 100% to 0% over a given period of time, either continuously, as a series of continuous slopes of varying steepness or sometimes in ratio steps. In such gradient mode, the viscosity of the mobile phase might also change dependent on the composition of the mobile phase. In the example of water and acetonitrile, viscosity of water is almost twice the viscosity of acetonitrile. A change in viscosity, however, also typically results in a change in the pressure required to drive the mobile phase through the stationary phase. When operating the mobile phase drive to maintain pressure, a reduction in viscosity allows increasing the flow rate, thus leading to shorter separation times.

Time-Base Control

In one embodiment, the HPLC system is controlled based on a clock cycle having a clock cycle period. The HPLC system might have one central clock or several clocks, with the clock cycle being derived from either the central clock or one of the several clocks. In most of today's applications, a method for running a certain separation is set up based on a constant flow rate. The method is then programmed with defined time marks for each method step.

In such embodiment of this invention, the clock cycle period is varied in dependence on the variation of a control value of the system. Such control value might be related to a property of the mobile phase, a pressure in the mobile phase, a pressure difference (preferably a pressure difference along the stationary phase or the separating device), a control parameter of the mobile phase drive (such as an electrical current, voltage and/or power for driving a pump), and/or a value related to the viscosity of the mobile phase at a given actual composition.

In one embodiment, the flow rate of the mobile phase is controlled by varying the clock cycle period in dependence on the variation in the control value. This allows to adapt methods designed e.g. for constant flow rate to embodiments of the present invention by varying the clock cycle period.

Internal Temperature Rise

Embodiments of the present invention might be controlled to achieve a constant internal temperature and/or constant internal temperature rise. With high restriction columns (e.g. packed with smaller dp, see http://hplc.chem.shu.edu/HPLC/glossary/g_pr.html, particles) simply the product of flow rate and pressure drop forms a hydraulic energy high enough to substantially raise the internal temperature of the column. Depending on the column geometry and material (thermal conductivity) this may result in substantial temperature gradient across (radial) and along (axial) the column. In this preferred embodiment the flow rate of the mobile phase is controlled such that either the hydraulic energy converted in the column is kept constant (see e.g. WO 2006032304 by the same applicant), or a measured temperature related signal is kept constant.

Apparatus

Embodiments of the present invention might be embodied based on most conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment comprises a pumping apparatus comprising a piston for reciprocation in a pump working chamber to compress liquid in the pump working chamber to a high pressure at which compressibility of the liquid becomes noticeable.

One embodiment comprises two pumping apparatuses coupled either in a serial or parallel manner. In the serial manner, as disclosed in the aforementioned EP 309596 A1, an outlet of the first pumping apparatus is coupled to an inlet of the second pumping apparatus, and an outlet of the second pumping apparatus provides an outlet of the pump. The teaching in the EP 309596 A1 with respect to the operation and embodiment of such serial dual pump shall be incorporated herein by reference. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (e.g. from the supply), thus allowing to provide a continuous flow at the output. However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column providing the stationary phase.

The mobile phase might comprise an organic solvent like e.g. methanol or acetonitrile, often diluted with water. For gradient operation water and organic are delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The pressure in the mobile phase might range from 200 to 2000 bar, and in particular 500 to 1500 bar.

The HPLC system might further comprise a sampling unit for introducing the sample fluid into the mobile phase stream, a detector for detecting separated compounds of the sample fluid, a fractionating unit for outputting separated compounds of the sample fluid, or any combination thereof. Further details of HPLC system are disclosed with respect to the Agilent 1200 Series Rapid Resolution LC system or the Agilent 1100 HPLC series, both provided by the applicant Agilent Technologies, under www.agilent.com which shall be incorporated herein by reference.

RS-Pumping, Gradient Transformation

In one embodiment, the HPLC system may comprise an isocratic system. Due to its inner volume the outflow may be disturbed when pressure changes. If e.g. at a sample injection the downstream system at least temporarily changes restriction, a constant flow operation will result in a corresponding pressure change. Such pressure changes, especially when being steep and/or dynamic, act on the compressible liquid in the inner volume. As a result the volumetric outflow is at least temporarily different to the displacement volume of the piston. Such difference may be called virtual flow, being subject to solvents in use, pump cycle phase, ambient temperature and technical elasticity of the pump hardware in use. This is different when operating the pump in a "pressure mode", where a change in pressure will be counteracted by a corresponding flow change, i.e. a change in the temporary flow rate. In best mode, no or substantially no virtual flow is introduced, but only an active displacement is controlled, which is precisely known in magnitude, e.g. simply by recording the motor movement.

In one embodiment, the HPLC system is a gradient system, being capable of blending solvents, often used in a time-programmed mode. Usually the term gradient defines ramping solvent composition, which is defined by entries in a so-called time-table (TTBL). A pumping system prepared for variable flow may need to translate such TTBL from the time-based regime into the volumetric regime, in particular in order to allow comparing the results of the separation such as retention times. It may calculate a volumetric table, generated from a time table with set flow as a known conversion factor. This way the volumetric table can be calculated as if the flow would have been left constant at the value given in the method. During execution the time table is no longer in effect. In minimum time slices the flow is converted (integrated) to form a "total pumped volume", which may then be e.g. the x-axis of a volumetric gradient program. As with any time point in-between regular time table entries, for any volume point in-between the converted entries the actual composition can be calculated. In principle, with constant flow operation, such program may form the identical gradient when measured over time. However, the advantage of this concept is that it may no longer be required to keep the flow constant. In a hierarchical approach a secondary timetable can be programmed to define flow changes over time. Still the volumetric composition will follow the gradient as originally programmed in a timetable with constant flow.

If it now is possible to define a flow change without influencing the gradient elution in terms of integral volume, peaks may still be reproducible when identified by retention volume instead of retention time. The relation of both can be the original setting for the constant flow mode.

If the execution of a gradient mode is independent of actual flow rate, this system can be enabled to be optimized for speed of analysis e.g. by tuning the flow rate such that a specific pressure is utilized. This may be the maximum pressure, which the system is able to take or generate. This can be done, for example, by reducing the flow rate when the pressure drop across a column is increased over time, which now allows running at or close to the limit of pressure capabilities. A measuring sequence need not be terminated, e.g. in case of an excessive increase in pressure drop, but the system can work at reduced flow rate settings.

Preferably, the HPLC system can tune the flow rate to (e.g. exactly) operate at a fixed pressure, independent of the actual viscosity. So at higher organic content (e.g. acetonitrile) the volumetric flow and thus the linear velocity can be increased. With a given pressure limitation this way the optimum of speed can be achieved, which in turn may lead to higher/maximum throughput under given run-time constraints.

During method development chromatographers can stay in "historic regimes", optimizing the gradient shape using constant flows. This may be easier to predict and work with, because prediction of separation is still easy. But during work horse times the instrument can perform optimized operation e.g. to utilize the utmost of separation speed (so-called "Rapid Separation"—RS—or RSLC).

To initiate speed enhancement in a preferred embodiment, the operator can switch to "RS-mode" e.g. with specifying an allowed system pressure. Even in an isocratic mode speed may be gained as the flow can go as high as the pressure limit allows.

Sometimes columns are operated at air under ambient conditions without an oven (purposely providing a defined temperature environment for the column in particular at temperatures at 10° and up to 100° C.) in place. Ambient temperature may influence viscosity e.g. by ~2%/° C. for aqueous liquids. So, for example, an estimated temperature drop of 5° C. during overnight operation may raise pressure by 10%.

In conventional HPLC systems operating under the constant flow rate maxim, an operator will usually stay away from pressure limits, at least at the beginning when starting a measuring sequence. During the course of consecutive runs the pressure drop may change. Also, the collection of dirt and particles may partly block the column frit over time, which simply means that the pressure rises over the course of multiple runs. In order to stay safe and not to interrupt the sequence by pressure errors, a user in conventional HPLC systems will typically leave a headspace of 10-20%. As such headspace is not required in embodiments of the present invention, this, in turn, can allow (e.g. already under stable conditions and isocratic operation) to increase speed of analysis by such headspace, e.g. about this 10-20%, even when no viscosity changes take place. Another advantage can be risk reduction connected to secured results. Instead of interrupting a sequence for pressure reasons, e.g. when a column is clogging slowly, embodiments of the present invention allow to continue with operation just at a lower speed.

The modern trend to sub-two micron packing material has allowed for more flexibility in selecting the flow rates. Flat Van Deemter curves indicate that resolution may be still acceptable at higher linear speeds and reproducible over volume when flow rates are increased or even modulated.

In one embodiment having a hierarchical approach, a flow timetable is executed as a real time program, while the composition timetable is executed as a volume based table. This way a variation in a control value in the system is determined once and the corresponding flow change now fed into the method.

Retention Volume

One embodiment of the present invention comprises determining (e.g. by an adequate analysis unit, which considers predicted, measured or elsewise derived flow information) a value of a retention volume representing such volume of the mobile phase required to elute a respective compound of the sample fluid at least through the separating device. The mobile phase drive is then operated (e.g. by an adequate control unit) based on the determined value of the retention volume. This makes use of the concept of retention volumes, rather than retention times, as shall be explained here in greater detail.

In conventional Liquid Chromatography (LC or HPLC), the data evaluation normally is based on a time axis. This is clearly visible in names, expressions and units, e.g. retention time (Rt), the run time at which the peak appeared in the detector, or peak area (usually determined in units of mAU*sec), integrated absorbance signal from peak begin to end. In most HPLC separations, it is a quality aspect to achieve reproducibility in the sub-digit percent range. This leads to the requirement that all influential factors are controlled to an even better precision.

While time based HPLC measurement appears to be easy, simply because it is a universally known and precisely measurable element, it may find its limitations when used for data evaluation. Only if volumetric flow rate of the mobile phase drive is known, constant and precise, there is a fixed time at which a certain peak (being related to a certain compound of the sample fluid) appears e.g. at the detector location. Same is true for quantitative results, which are concentrations calculated from peak areas.

In older days the signal of an HPLC-detector used to be an analog output signal. This signal was routed to a kind of strip chart recorder, which started the recording on a trigger pulse from the injection valve. In order to gain precise timing of the peak appearing (Rt) on the chart, the flow rate had to be precisely known, especially when comparing results from different systems.

Retention time not only is dependent on flow rate, but also dependent e.g. on type and geometry of the stationary phase (e.g. the column), its temperature and the mobile phase composition. While the stationary phase type and geometry are pretty stable parameters, temperature, solvent composition and flow rate may show variances. It used to be mandatory to use precision hardware and feedback control in order to precisely define these parameters during analytical runs.

It is good laboratory practice to ensure adequate performance through operational qualification or even system suitability testing. But often individual parameters are not controlled directly because adequate sensors are not available, or sometimes feedback control is instable or too slow and/or often too expensive.

According to embodiments of the present invention, for the concept of retention volumes certain (preferably all) instrument components distribute their internal data to the analysis unit. This data will then be used to extract analysis results. Especially the mobile phase drive (e.g. pump system) may not just generate a pressure trace for monitoring, but it may also have a data channel for flow rate and other relevant information, e.g. solvent composition, integral volume. Analytical data from the separating device (e.g. column) can be added, such as retention factor and elution strength across solvent composition. Data evaluation may now consider such additional traces to adapt to run-time conditions and correlate results to correct for changes.

Considering a pressure ripple, for example, such ripple may be acceptable at a level of 5-10%, if solvent composition is still accurate. But with conventional peak area calculation based on time, normal peak integration now calculates different concentrations, if the peak elutes on the high part of the ripple as compared to during the low portion.

Flow rate in a first approximation is a direct result of applied pressure, which means that—in case of a pressure ripple—the flow rate has a ripple too. E.g. with a 2% higher flow rate the peak area (usually determined in units of mAU*sec) is calculated to be 2% lower. Considering absorbance as a concentration dependent signal, intensity (e.g. peak height) is not changed, but the peak distribution in time depends on substance speed. Higher flow rate makes the substance pass by the detector at a higher linear speed, making it look narrow, resulting in lower peak area reading.

Preferred embodiments may comprise precise flow measurement allowing to precisely measure and/or determine the flow rate (usually determined at a certain point within the flow path of the mobile phase). Distributing such data all the way to the analysis unit may support more functions beyond monitoring, diagnostics and/or error handling. If such flow data is incorporated, retention based on actual volume can be calculated. A peak can then be identified by its characteristic retention volume (in combination with or instead of the corresponding retention time). Such a flow measurement device may be embodied as described under EP 1777515 A or US 2008-0022765 A1, the teaching of those documents with respect to flow measuring devices being incorporated herein by reference.

In order to connect to existing data analysis tools like LC-Integrators, embodiments may combine the individual data for e.g. absorbance and flow into a one dimensional structure. As a simple example the absorbance vs. time can be combined with flow vs. time to form a trace for absorbance vs. volume. Assuming an artificial but constant flow value such absorbance vs. volume can easily be back-translated into absorbance vs. time to allow handling the data by conventional systems (e.g. integrators). Such processing may be an integral function of e.g. absorbance detectors, which then receive flow readings from a pump system or separate flow sensor to perform the translation before a raw data file is generated.

In one embodiment, the retention volume is related to a respective condition derived e.g. from a previous calibration, a previous reference analysis, or by referencing to a result from a previous analytical run.

In one embodiment, the retention volume is related to elution strength of the system. The elution strength may be determined by at least one of temperature, mobile phase composition, and characteristic of at least one of the stationary phase, the separating device, and the elution strength across solvent composition, say 'absorption isotherm' of the sample component of interest. Such runtime parameters can either be measured directly or predicted from measurements or models. This way the data evaluation corrects for slight deviations of relevant operating parameters, e.g. at higher temperature and/or organic content sample components may be eluted at lower volumes.

In one embodiment, the retention volume is related to a volume of a solvent component of the mobile phase. The volume may be a volume over time in particular in case the volume of the solvent component varies over time. This relates to a system comprising two or more separated mobile phase drives for e.g. water and organic solvents. Instead of identifying peaks by elution volume at specific organic composition it may be of advantage to integrate individual flows of the separate mobile phase.

In one embodiment, the retention volume is related to a total volume of the mobile phase comprising one or more different solvent components. The total volume may be a flow rate integrated over time in particular in case the flow rate varies over time.

The value of retention volume may be determined based on a value of flow rate integrated over time, preferably integrated over a period of time related to an introduction of the sample fluid into the mobile phase and an elution of at least one compound of the sample fluid from the stationary phase, because this describes the amount of liquid required to transport that sample compound through the separating device.

Alternatively or in combination, the value of retention volume may be determined based on a composition (or a variation over time of a composition) of the mobile phase being comprised of a plurality of solvent components, preferably a variation over time of a ratio of the plurality of solvent components.

Alternatively or in combination, the value of retention volume may be determined based on a temperature of the mobile phase in the separating device, preferably a variation over time of the temperature. Especially when normal sized separating devices (4.6 mm columns) are filled with small particle packings running at higher pressures may increase the inner temperature due to frictional heating (inner temperature rise).

Generally speaking it has to be understood that the term "retention time" is defined by the actual time measured (e.g. when a certain peak occurs) in combination with a method defining the mode of separation. That means that different methods can lead to different retention times for the same component. Accordingly, the term "retention volume" is defined by the actual volume of mobile phase, as calculated and/or measured (e.g. when a certain peak occurs) in combination with a method defining the mode of separation, so that different methods can lead to different retention volumes for the same component. This applies in particular in gradient modes, wherein retention is strongly dependent on the actual ratio of solvents forming the mobile phase.

Embodiments of the invention can be partly or entirely embodied or supported by one or more suitable software programs, which can be stored on or otherwise provided by any kind of data carrier, and which might be executed in or by any suitable data processing unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

FIG. 5 shows an example of a composition gradient.

FIGS. 6A-6F illustrate time domain and volume domain analysis.

In FIG. 1, a pump 20, as a mobile phase drive and which might be embodied as illustrated in FIGS. 2-3, drives a mobile phase through a separating device 30 (such as a chromatographic column) comprising a stationary phase. A sampling unit 40 can be provided between the pump 20 and the separating device 30 in order to introduce a sample fluid to the mobile phase. The stationary phase of the separating device 30 is adapted for separating compounds of the sample liquid. A detector 50 is provided for detecting separated compounds of the sample fluid. A fractionating unit 60 can be provided for outputting separated compounds of sample fluid.

Figure 1:
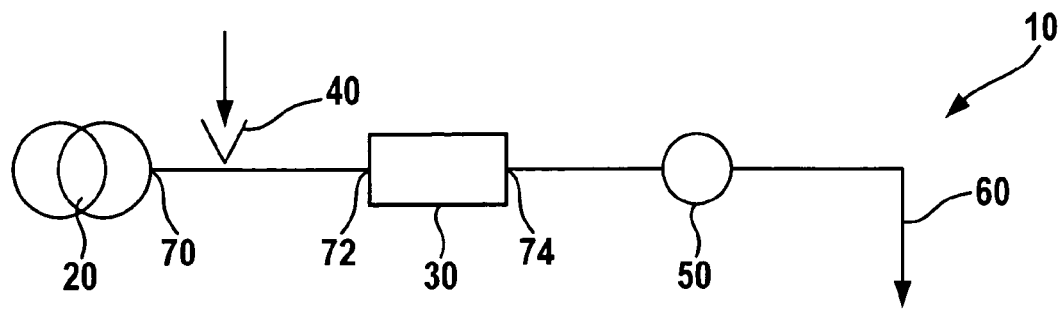
FIG. 1 shows a liquid separation system 10, in accordance with embodiments of the present invention, e.g. used in high performance liquid chromatography (HPLC).
Figure 2:
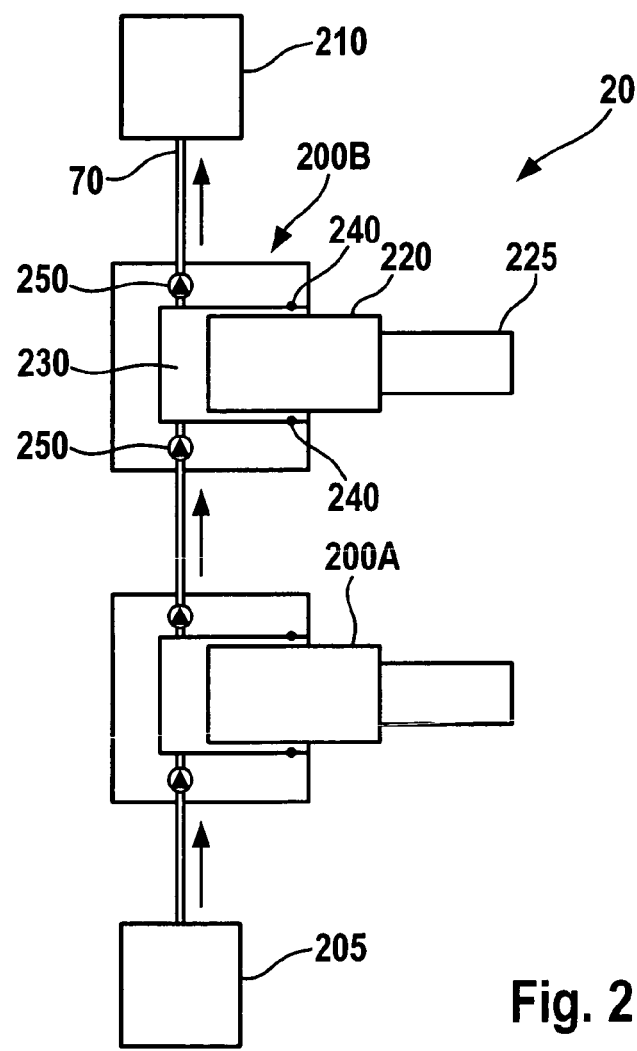
FIGS. 2-3 show basic embodiments of the pump 20.

In the serial dual piston pump of FIG. 2, a first pumping apparatus 200A is coupled at its input to a liquid supply 205 (which may be one or more liquid reservoirs, e.g. in order to allow comprising the mobile phase of plural different solvents which composition might be controlled to vary over time as in a gradient mode), and its output is coupled to the input of a second pumping apparatus 200B. In order to provide a continuous flow of liquid, the pump volume of the first pumping apparatus 200A might be embodied larger than the pump volume of the second pumping apparatus 200B, so that the first pumping apparatus 200A will supply a portion of its displaced volume directly into a system 210 (which can be the system 10 of FIG. 1, of course, without the pump 20) and the remaining portion to supply the second pumping apparatus 200B on its backstroke, which will then supply the system 210 on its forward stroke during the intake phase of the first pumping apparatus 200A. The ratio of the pump volume of the first pumping apparatus 200A to the second pumping apparatus 200B is preferably 2:1, but any other meaningful ratio might be applied accordingly. Further details about the configuration and construction of the pump as well as the operation mode of such dual serial pump are disclosed in the aforementioned EP 309596 A1 and shall be incorporated herein by reference.

Figure 3:
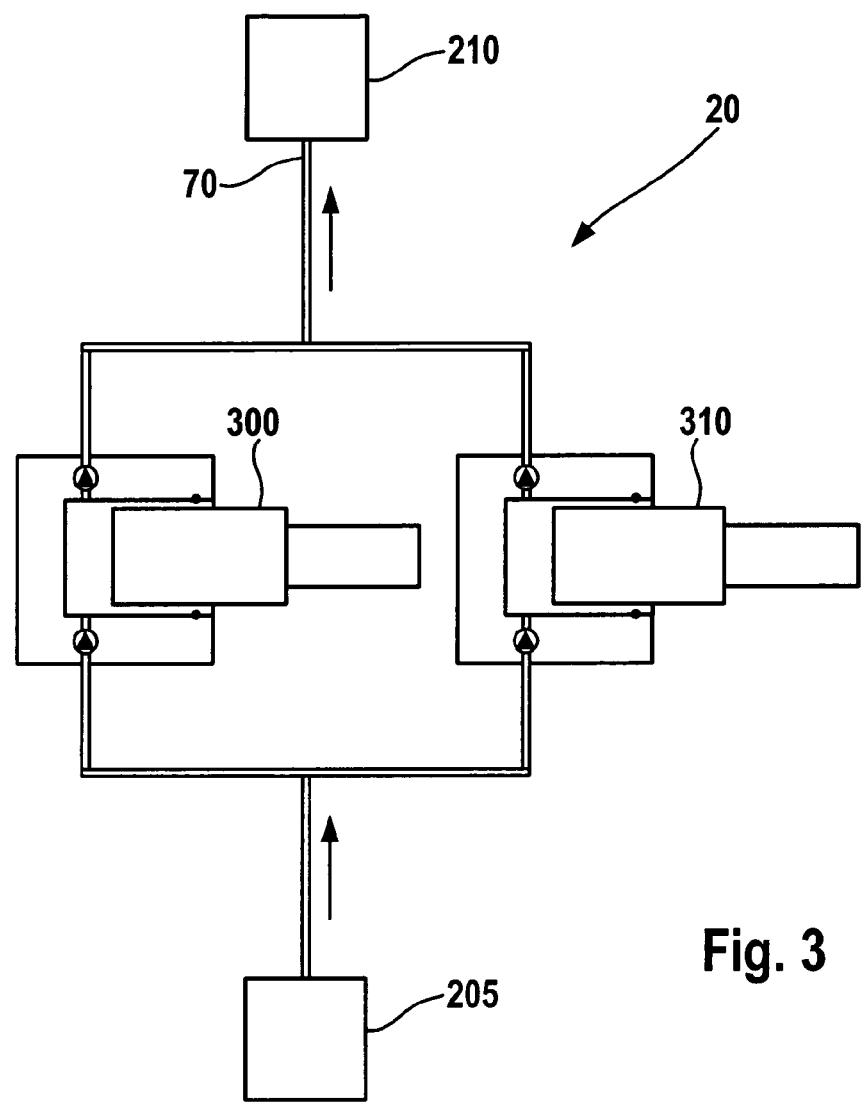

In the parallel dual pump of FIG. 3, the inputs of a first pumping apparatus 300 and a second pumping apparatus 310 are coupled in parallel to the liquid supply 205, and the outputs of the two pumping apparatuses 300 and 310 are coupled in parallel to the system 210 receiving the liquid at high pressure. The two pumping apparatuses 300 and 310 are operated usually with substantially 180 degree phase shift, so that at any time only one pumping apparatus is supplying into the system while the other is intaking liquid from the supply 205. However, it is clear that also both pumping apparatuses 300 and 310 might be operated in forward stroke in parallel (i.e. concurrently), at least during certain transitional phases e.g. to provide a smooth(er) transition of the pumping cycles between the pumping apparatuses.

As illustrated in principle in the FIGS. 2 and 3, each of the pumping apparatus 200A, 200B, 300, and 310 is preferably configured as a reciprocating pump. As exemplarily illustrated in FIG. 2 with respect to the pumping apparatus 200B, the pumping apparatus 200B comprises a piston or plunger 220 (typically driven by a not shown drive which might be coupled to the piston 220 by a piston rod 225) arranged to perform reciprocal movements in a corresponding pump working chamber 230, thereby compressing the liquid within the pump working chamber 230 during its forward stroke. One or more seals 240 might be used to seal in particular the moving parts such as the piston 220 against the pump working chamber 230. Further, one or more valves 250 can be used to control the direction of the liquid flow. The pressure applied by the pumps 20 usually ranges about 200-1000 bar and beyond up to currently even 2500 bar. Compressibility of the liquid at such pressure becomes noticeable and might lead to pulsation effects, which have to be encountered. Typical flow rates are in the range of microliters to milliliters per minute.

Turning again to FIG. 1, according to embodiments of the present invention, the flow rate of the mobile phase can be controlled in dependence on a variation in a control value related e.g. to a pressure in the mobile phase, thus allowing to vary the flow rate in response to variations in the mobile phase (e.g. pressure). For that purpose, the system 10 can be designed to be essentially self-controlled or free-wheeling, so that a variation in pressure "automatically" leads to a variation in flow rate. This can be achieved e.g. by (passively) operating the pump 20 to be free-wheeling, so that the pump 20 is running at a given power (e.g. maximum power). In such case, a variation in the mobile phase pressure will in turn lead to a variation in flow rate. For example when the pressure decreases, the free-wheeling pump 20 will then increase speed and thus the flow rate, as it can then run faster at the same power consumption.

Figure 4A:
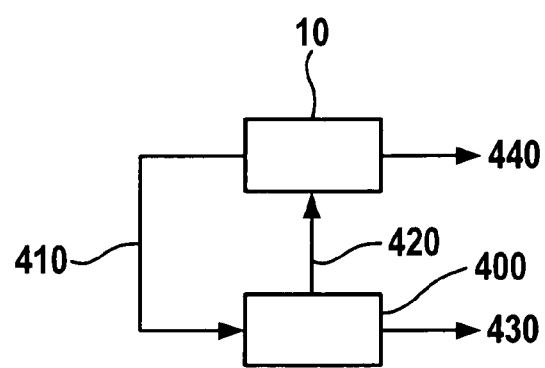
FIG. 4A shows an embodiment with active operation, and FIG. 4B indicates a variation of the flow rate in response to a change in pressure.

FIG. 4A shows an alternative embodiment, wherein the pump 20 is actively operated to drive the mobile phase at a flow rate in dependence on the variation in the control value. A control unit 400 actively controls e.g. the pump 20 to vary the flow rate in response to a variation in the mobile phase pressure. In FIG. 4, the control unit 400 is coupled to the liquid separation system 10 to receive (reference numeral 410) data from the system 10 and to control (reference numeral 420), in turn, the system 10. Either the system 10 or the control unit 400, or both, might comprise a data output, represented in FIG. 4 by reference numeral 430 for the data output of the control unit 400 and reference numeral 440 for the data output of the system 10.

In the embodiment of FIG. 4A as well as the case of free-wheeling, the mobile pump 20 is operated to reduce the flow rate in response to an increase of the control value, and to increase the flow rate in response to a decrease of the control value. Such reduction and increase of the flow rate can be in relation to a given value of the flow rate, such as a defined flow rate value for a certain type of chromatographic column 30.

In case the pump 20 is working in cyclic manner (as in the embodiments of FIGS. 2 and 3), a cycle period (when delivering the mobile phase) results from reciprocating movement of the piston 220. In a preferred embodiment the pump 20 is operated to respond only to such variation in the control value having a time constant larger than the cycle period. Thus, it can be ensured that the flow rate is not following pressure variations caused by the pump 20 itself. The time constant is preferably selected to be larger than ripples or pulsation resulting from the cycling operation of the pump 20.

Figure 4B:
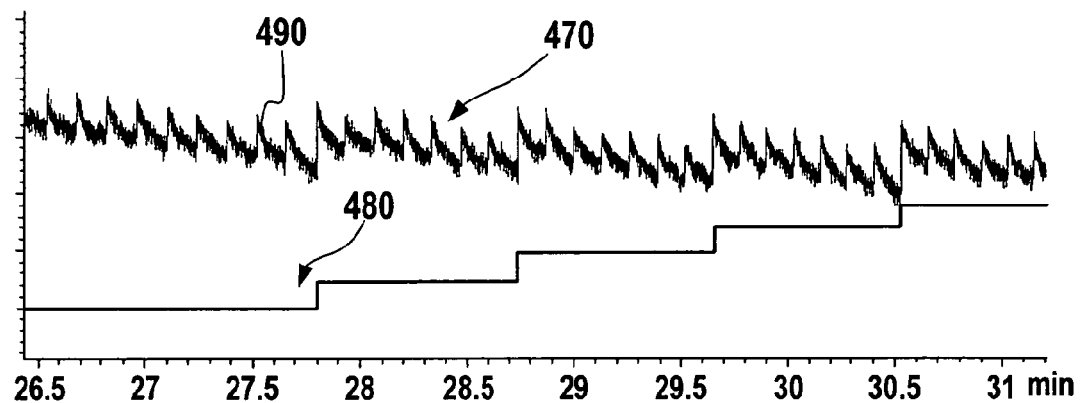

FIG. 4B shows an example, wherein the pressure 470 decreases over time, and the flow rate 480—in turn—is increased over time. In this example, the time constant for varying the flow rate 480 (as indicated by the stepwise increase) is selected to be larger than ripples or pulsation (reference numeral 490 indicating such ripple) resulting from the cycling operation of the pump 20.

The flow rate of the mobile phase can be determined at an outlet 70 (cf. FIGS. 1-3) of the pump 20, before (reference numeral 72 in FIG. 1) passing the column 30, after (reference numeral 74 in FIG. 1) passing the column 30, an outlet of the high performance liquid chromatography system such as the fractionator 60, or any combination thereof.

The control unit 400 (FIG. 4A) receives (reference numeral 410) from the HPLC system 10 the control value, which is or is related e.g. to a pressure in the mobile phase. While the control value is preferably an actually measured value, such as the pressure (e.g. by any kind pressure sensor as known in the art—not shown in the figures), in the mobile phase, it is to be understood that any other parameter showing a dependency on a mobile phase property can serve as such control value when used to control the flow rate. Examples can be a pressure difference e.g. along the column 30 (e.g. measured for example between 72 and 74), or a value related to a viscosity of the mobile phase.

Alternatively, the control value can be derived from a control parameter of the pump 20 such as an electrical current, voltage and power for driving the pump 20. A variation in current, voltage or power for driving the pump 20 is usually indicative of the load of the pump 20 or in other words of the pressure drop required for driving the mobile phase through the stationary phase in the separating device 30.

As the mobile phase is "distributed" and also varies (e.g. in pressure) all along the HPLC system 10 (e.g. the pressure at point 72 is the "system pressure" provided by the pump 20, e.g. 600 bar, while the pressure after the column 30 at point 74 is substantially ambient pressure), there are many options with respect to the location at which the control value is related. Such location can be the outlet 70 of the pump 20, the injection point of the sampling unit 40, the entrance area 72 of the column 20, preferably the head of column, the exit area 74 of the column 20, etc. or combinations thereof.

In a preferred embodiment, the control unit 400 operates the pump 20 to maintain the control value to be substantially constant or at least within a given range, so that the pump 20 will deliver the mobile phase (e.g. at the output 70) at a certain pressure, such as e.g. the maximum achievable pressure of the pump 20 with or without a certain safety margin. Such operating at a constant/maximum pressure, in turn, can lead to reduced analysis times, as will be shown later, in particular when running the HPLC system in a gradient mode, i.e. when composition of the mobile phase varies over time. In gradient mode, the mobile phase comprises different solvent components with the ratio of the different solvent components being varied over time.

FIG. 5 shows an example of a composition gradient of water and acetonitrile, with ratio of water to acetonitrile being varied stepwise from 100% to 0% over a given period of time. The x-axis shows the time in units of minute, and the y-axis depicts the pressure (at the output 70 of the pump 20) required to drive the mobile phase through the system 210. The numbers below each gradient step indicate the percentage of acetonitrile in water, so that in this example at time 0 the mobile phase is 100% water, after 6 minutes the ratio is 50% water and 50% acetonitrile, and at 11 minutes the mobile phase is 100% acetonitrile. In this gradient example, the viscosity of the mobile phase also changes. Viscosity is dependent on the composition of the mobile phase. This can be seen in FIG. 5 from the change in the pressure required to drive the mobile phase at a constant flow rate. As apparent from FIG. 5, the pressure to drive pure water is more than twice the pressure to drive pure acetonitrile; accordingly the viscosity of water is more than twice the viscosity of acetonitrile.

When operating the pump 20 to provide a substantially constant output pressure, a reduction in viscosity—in turn—results in increasing the flow rate, thus leading to shorter separation times, as shall be illustrated in the following with respect to FIGS. 6A-6F. FIG. 6A depicts the course of an exemplary composition gradient showing the percentage of solvent B over the time t. FIG. 6B shows the same composition gradient as in FIG. 6A, however depicted as percentage of solvent B over the volume V of the mobile phase flowing e.g. at point 74 after the column 30. In other words, assuming a given flow value allows to translate 6A to 6B, FIG. 6A shows the gradient in "time domain" while FIG. 6B shows the gradient in "volume domain".

FIG. 6C shows the course of the viscosity q for the gradient of FIG. 6A, which also corresponds to the pressure P required to drive the mobile phase. While the solid line depicts the course of the pressure P in case the flow rate is kept constant (as this would be the preferred mode of operation in most prior art systems following the constant flow rate paradigm), the area between the dotted and the solid line indicates the "potential" or "unused" pressure resource.

For the sake of reference, time tf shall represent the point in time when an HPLC analysis method programmed according to FIG. 6A and operated at constant flow rate shall be finished. At the time tf, a volume V0 of mobile phase has passed the column 30 and shall represent the volume of mobile phase (as defined by a specific HPLC method) to elute the sample fluid from the column 30.

According to embodiments of the present invention, the pump 20 is operated to supply at maximum pressure thus following the dotted line in FIG. 6C. Accordingly, the flow rate for the dotted course in the example of FIG. 6C does not remain constant but basically follows as shown by the dotted course in FIG. 6F. FIG. 6F depicts the course in principle of the flow rate Q over the time t. The straight line in FIG. 6F shows the flow rate following the constant flow rate paradigm, which corresponds to the solid line course of the pressure in FIG. 6C. The area between the dotted and the straight lines in FIG. 6F can also be interpreted as "room for speed up" the HPLC analysis over the constant flow rate paradigm.

In the volume domain representation, FIG. 6E depicts the executed flow or possible flow Q over the volume V, whereat V0 represents the area under the straight line course in FIG. 6C.

FIG. 6G eventually shows the course (percentage of solvent B) over the time t of the composition gradient corresponding to the dotted lines in FIGS. 6C and 6F. The time tv indicates the point in time, when the volume V0 of mobile phase has passed the column, which is the same volume as passing the column 30 according to the course of FIG. 6F until the point in time tf. As the flow rate has been increased with respect to the straight line course of FIG. 6F, tv occurs before tf, so that a time difference tf–tv represents the speed improvement as indicated by arrow 600.

The volume V0 is indicated in FIG. 6F as shaded area underneath the curve until tf.

RS-Pumping

In one embodiment, the control unit 400 calculates a volumetric table, generated from a time table with flow setpoint as a known conversion factor. During execution the time table is no longer in effect. In minimum time slices the flow is converted (integrated) to form a "total pumped volume", which may then be e.g. the x-axis of a gradient program being active in the volume-domain. As with any time point in-between entries (i.e. supporting points) of the time table, for any volume point in-between the converted entries the actual composition can be calculated. In principle, with constant flow operation, such program may form the identical gradient. However, the advantage of this concept is that it may no longer be required to keep the flow constant. In a hierarchical approach a secondary time table can be programmed to define flow changes over time. Still the volumetric composition will follow the gradient as originally programmed in a time table with constant flow. In this volume domain it now is possible to define a flow change without influencing the gradient elution in terms of integral volume, peaks may still be reproducible when identified by retention volume instead of retention time. The relation of both can be the original flow setting for the constant flow mode.

Retention Volume

In one embodiment the control unit 400 determines a value of a retention volume representing such volume of the mobile phase required to elute a respective compound of the sample fluid at least through the separating device. With respect to the examples in FIG. 6, the volume V0 represents such (entire) retention volume. The pump 20 is then operated (e.g. by the control unit 400 or by being operated to be free-wheeling) based on the determined value of the retention volume, meaning that the analytical run is stopped when V0 is passed. Instead of being terminated by the setting of 'stop time' the actual run terminates on reaching a 'stop volume'.

In order to determine the current value of retention volume, the control unit 400 receives certain internal data (such as current flow rate, control value, temperature, solvent composition, and integral volume) from the components of the system 10. It is clear that in many cases the more data the control unit 400 receives the more accurately the retention volume can be determined. The pump 20 may generate a pressure trace for monitoring together with the values of flow rate and other relevant information, e.g. solvent composition, integral volume. Analytical data from the column 30 can be added, such as retention factor and elution strength across solvent composition. The control unit 400 can then consider such additional traces to adapt to run-time conditions and correct for changes.

The control unit 400 may combine individual data for e.g. absorbance (as received from the detector 50) and flow (as received from the pump 20) into a one dimensional structure. The absorbance vs. time can be combined with flow vs. time to form a trace for absorbance vs. volume. Assuming an artificial but constant flow value, the control unit 400 can "back-translate" such absorbance vs. volume into absorbance vs. time.

Time-Base Control

Figure 7:
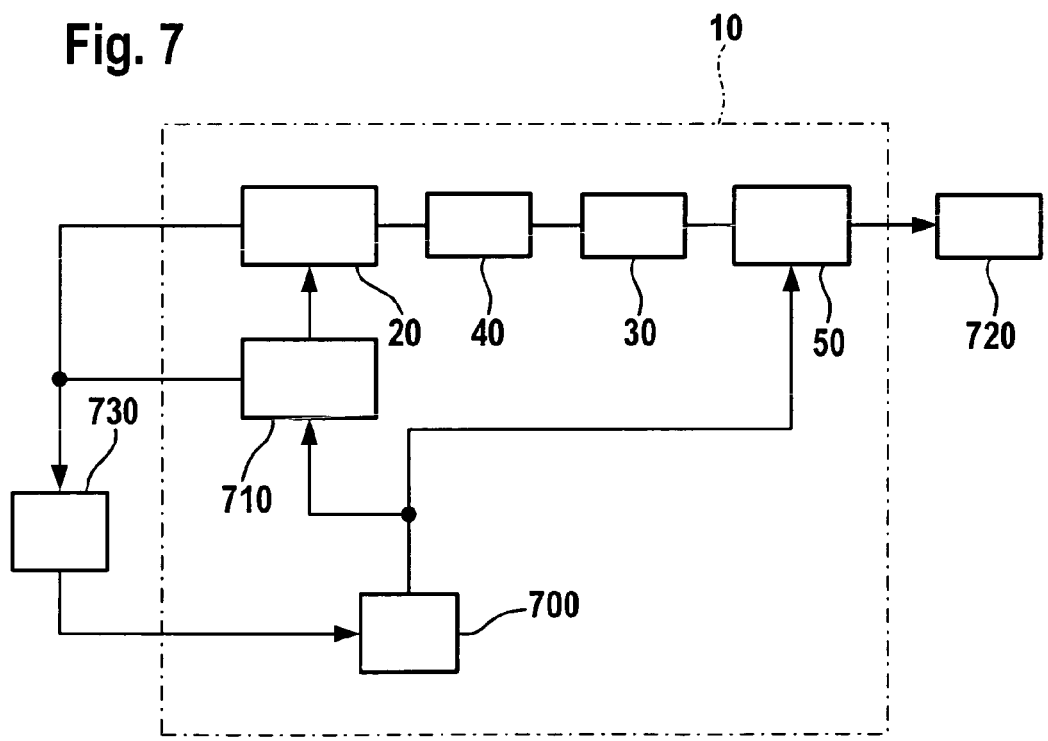
FIG. 7 shows an embodiment, wherein the HPLC system 10 is controlled based on a clock cycle having a variable clock cycle period.

FIG. 7 shows an embodiment, wherein the HPLC system 10 is controlled based on a clock signal having a variable clock cycle period. The HPLC system 10 has a central clock 700 feeding—in this example—the clock signal to a pump control unit 710 (for controlling the pump 20) as well as to the detector 50. It is clear that the clock 700 might also feed other units, which however is not shown here.

During operation, the HPLC system 10 runs an analytical method, as known in the art, with the operation of the pump 20 as well as of the detector 50 being controlled by the clock 700. The detector 50 may provide output data to a data analysis unit 720, such as a PC, workstation or any other kind of data processing unit, for further processing such output data. In so far, the embodiment of FIG. 7 substantially represents an HPLC system e.g. as the aforementioned Agilent 1200 Series Rapid Resolution LC system.

The embodiment of FIG. 7 further comprises a clock control unit 730 receiving from the pump 20 and/or the pump control unit 710 a control value related to a pressure of the mobile phase as provided by the pump 20. Such control value might be the actual pressure measured e.g. at the outlet 70 (cf. FIG. 1) of the pump 20, or the set pressure as the pressure output to which the pump control unit 710 is controlling the pump 20.

Based on the received control value, the clock control unit 730 varies the clock cycle period of the clock 700. In a preferred embodiment, when the control value indicates that the pressure of the mobile phase (e.g. at the outlet 70) differs from a set pressure value (e.g. the maximum pressure of the pump 20), the clock control unit 730 varies the clock cycle period until the set pressure value is reached (at least within a certain range). E.g. in case the control value indicates that the pressure of the mobile phase is lower than the set pressure value, the clock control unit 730 decreases the clock cycle period (i.e. increases the clock cycle frequency) until the set pressure value is reached (at least within a certain range). Accordingly, when the control value indicates that the pressure of the mobile phase is higher than the set pressure value, the clock control unit 730 increases the clock cycle period (i.e. decreases the clock cycle frequency) until the set pressure value is reached (at least within a certain range).

Alternative to the concept of one central clock 700, the HPLC system 10 might have several clocks, with the clock cycle being derived from either the central clock 700 or one of the several clocks.

One advantage of the embodiment of FIG. 7 is that it allows running conventional constant-flow-rate based methods as well as variable flow rate methods (according to the present invention) on the same system 10. Even more, it allows using even the very same method in either constant-flow-rate mode or in variable flow rate mode (according to the present invention). Accordingly, methods which might have been designed under the constant-flow-rate paradigm are run in the variable flow rate mode in exactly the same way as in the constant-flow-rate mode, with the only difference that the clock cycle period is varied in the variable flow rate mode. As the clock frequency is usually increased in the variable flow rate mode, at least temporarily, this can mean that the measuring results will be provided faster than in the constant-flow-rate mode. Both results (i.e. measuring results for one method run in either constant-flow-rate or variable flow rate mode) are directly comparable and should in best case even be identical. Variations between results from either mode can result e.g. from temperature effects, when pressure conditions result in significant modifications of solvent behavior or changes of elution strength, or when running a too slow linear speed, so that the instrument is operated in the steep portion of the van Deemter curve.

In case the flow rate is at least temporarily increased in the variable flow rate mode, the measuring results will occur faster. In case a method is run which has been designed for constant-flow-rate mode, this might lead to the situation that a measuring result occurs faster than the time stamp assigned to such measuring result. In an example, a peak in variable flow rate mode occurs after 3 min, but as the method has been designed in constant-flow-rate mode, the peak bears the time stamp 4 min. That means that if that method had been run in constant-flow-rate mode, the peak would have occurred after 4 min. Thus peaks in variable flow rate mode can be actually analyzed faster than their time stamp, or in other words, the same measuring results (in ideal case) occur faster or the method can be run faster.

In most of today's applications, a method for running a certain separation is set up based on a constant flow rate. The method is then programmed with defined time marks for each method step. Without any further treatment or modification of the programmed timetable it is possible e.g. to adjust the gradient timing for variations in flow rate. In the embodiment of FIG. 7, the central clock 700 is defined as the clock of the pump system 20. If for e.g. 1 ml/min flow rate a clock cycle period were 1 msec (1 kHz), a simple linear relation (2 kHz for 2 ml/min) will change this clock to correct the execution of timetable. With higher flow rate the clock is running faster. This way the clock is running in flow*time, which actually is a volume ticker. If flow rate is implemented in a form of x many steps per ticker, then this automatically adjusts flow when the clock rate is adjusted depending on pressure.

In such embodiment, the flow rate of the mobile phase can be controlled by varying the clock cycle period in dependence on the variation in the control value. This allows to adapt methods designed e.g. for constant flow rate to embodiments of the present invention by varying the clock cycle period.

A further advantage of such an embodiment is the automatic correction resulting in data analysis, which now only requires distributing the pump ticker as master clock also to the detection device 50. Usually such a detection device 50 delivers raw data at a fixed data rate. According to this invention this data rate now is preferably derived from the distributed pump ticker, which in turn represents each data point as per volume concentration.

A simple "rule of thumb" might be used: at twice the nominal flow rate data points come at twice the nominal speed. If interpreted the regular way (data points at fixed time slices) retention times are calculated to be twice the actual time. This way any regular data evaluation tool can be ready to work with variable flow control according to this invention. For correct peak identification only the detection device needs to work on the flow ticker of the pump module.

As a side effect, any 'stop time' setting, usually used to terminate the analytical run, can be based on this flow ticker, resulting in terminating the run at a specific volume, instead of at a fixed time. It has to be understood that now an e.g. 2 min runtime can be executed in 1 min, if achievable flow rate is twice the nominal value. Still the result is displayed as a 2 min data trace, if a regular data evaluation tool is used.

The invention claimed is:

1. A high performance liquid chromatography (HPLC) system, comprising:
   a separating device comprising a separating device inlet, a separating device outlet, and a stationary phase for separating compounds of a sample fluid carried in a mobile phase;
   a mobile phase drive comprising a mobile phase drive outlet in fluid communication with the separating device inlet, the mobile phase drive configured for driving the mobile phase through the separating device at a fluid pressure and a fluid flow rate; and
   a control unit in signal communication with the mobile phase drive, the control unit configured for:
   receiving a control value indicative of the fluid pressure in the mobile phase; and
   based on the control value, maintaining the fluid pressure at the separating device inlet substantially at a set value or within a range including the set value, by controlling the mobile phase drive to vary the fluid flow rate,
   wherein the control value is selected from the group consisting of:
   a pressure measured in the mobile phase;
   a pressure difference between the separating device inlet and the separating device outlet;
   a control parameter of the mobile phase drive;
   a temperature measured in the mobile phase; and
   a combination of two or more of the foregoing.

2. The HPLC system of claim 1, wherein the control unit comprises an analysis unit configured for determining a value of a retention volume representing such volume of the mobile phase required to elute a respective compound of the sample fluid at least through the separating device.

3. The HPLC system of claim 1, comprising a feature selected from the group consisting of:
   the separating device comprises a chromatographic column providing the stationary phase;
   the mobile phase drive is configured for driving the mobile phase as a mixture of solvents, wherein a viscosity of the mixture changes as a composition of the mixture changes;
   an injector configured for injecting the sample fluid into the mobile phase, wherein the sample fluid comprises a matrix, and wherein a viscosity of the matrix is substantially higher than a viscosity of the mobile phase, resulting in an at least initial increase in pressure drop across a portion of the HPLC system downstream from the mobile phase drive;
   the fluid pressure is in a range from 200 to 2000 bar; and
   a combination of two or more of the foregoing.

4. The HPLC system of claim 1, wherein:
   the mobile phase comprises a plurality of different solvents;
   the mobile phase drive is configured for driving the mobile phase through the separating device according to a gradient mode in which a compositional ratio of the solvents in the mobile phase varies over time; and
   the control unit is configured for maintaining the fluid pressure at the separating device inlet substantially at a set value or within a range including the set value while the compositional ratio of the solvents in the mobile phase varies over time.

5. The HPLC system of claim 4, wherein the control unit is configured for controlling the mobile phase drive to increase the fluid flow rate while the compositional ratio of the solvents in the mobile phase varies over time, in response to the control value decreasing.

6. The HPLC system of claim 1, wherein the control value comprises at least the pressure measured in the mobile phase, and the pressure measured in the mobile phase is selected from the group consisting of:
pressure measured at the mobile phase drive outlet;
pressure measured at a sample injection point between the mobile phase drive outlet and the separating device inlet;
pressure measured at the separating device inlet;
pressure measured at the separating device outlet;
pressure measured at an outlet of the HPLC system downstream from the separating device outlet; and
a combination of two or more of the foregoing.

7. The HPLC system of claim 1, wherein the control value comprises at least the control parameter of the mobile phase drive, and the control parameter of the mobile phase drive is selected from the group consisting of:
electrical current supplied to the mobile phase drive for driving the mobile phase drive;
voltage supplied to the mobile phase drive for driving the mobile phase drive;
electrical power supplied to the mobile phase drive for driving the mobile phase drive; and
a combination of two or more of the foregoing.

8. The HPLC system of claim 1, wherein:
the control unit is configured for controlling the mobile phase drive to vary the fluid flow rate according to a tunable clock cycle period; and
the control unit comprises a clock control unit configured for receiving the control value and, based on the control value, varying the clock cycle period.

9. A high performance liquid chromatography (HPLC) system, comprising:
a liquid supply configured for supplying a plurality of different solvents comprising at least a first solvent and a second solvent, the first solvent and the second solvent having different viscosities;
a chromatographic column comprising a column inlet, a column outlet, and a stationary phase between the column inlet and the column outlet, the stationary phase configured for separating compounds of a sample fluid carried in a mobile phase comprising a mixture of the first solvent and the second solvent;
a pump in fluid communication with the liquid supply and comprising a pump outlet in fluid communication with the column inlet, the pump configured for driving the mobile phase through the chromatographic column at a fluid pressure and a fluid flow rate;
a pressure sensor configured for outputting a pressure measurement signal indicative of the fluid pressure at the column inlet; and
a control unit in signal communication with the pump and the pressure sensor, the control unit configured for:
controlling the pump to drive the mobile phase through the chromatographic column according to a gradient mode in which a compositional ratio of at least the first solvent and the second solvent in the mobile phase varies over time and a viscosity of the mobile phase varies over time;
receiving the pressure measurement signal; and
based on the pressure measurement signal, maintaining fluid pressure at the column inlet substantially at a set value or within a range including the set value, by controlling the pump to vary the fluid flow rate while the compositional ratio and the viscosity of the mobile phase vary over time.

* * * * *